United States Patent [19]

Muz

[11] Patent Number: 4,842,557
[45] Date of Patent: Jun. 27, 1989

[54] CONTACT DEVICE FOR MAKING AN ELECTRICALLY CONDUCTIVE CONNECTION

[75] Inventor: Edwin Muz, Reutlingen, Fed. Rep. of Germany

[73] Assignee: Nicolay GmbH, Kirchheim, Fed. Rep. of Germany

[21] Appl. No.: 203,073

[22] Filed: Jun. 7, 1988

[30] Foreign Application Priority Data

Jun. 11, 1987 [DE] Fed. Rep. of Germany ....... 3719474

[51] Int. Cl.⁴ ............................................. H01R 11/22
[52] U.S. Cl. ..................... 439/851; 439/860; 439/883; 439/736
[58] Field of Search ............... 439/859, 860, 883, 867, 439/868, 592, 593, 833, 818, 821, 823, 433, 434, 828, 842, 848, 838–841, 736, 850, 851

[56] References Cited

U.S. PATENT DOCUMENTS

| | | | |
|---|---|---|---|
| 1,965,270 | 7/1934 | Werner | 439/859 |
| 2,235,780 | 3/1941 | Wagstaff | 439/842 |
| 2,708,266 | 5/1955 | Pavlinetz | 439/434 |
| 3,569,919 | 3/1971 | Daddona et al. | 439/848 |
| 3,665,373 | 5/1972 | Voglesonger | 439/439 |
| 3,728,669 | 4/1973 | Churla | 439/860 |

FOREIGN PATENT DOCUMENTS

| | | | |
|---|---|---|---|
| 876857 | 5/1953 | Fed. Rep. of Germany | 439/859 |
| 3106594 | 9/1982 | Fed. Rep. of Germany | |
| 162804 | 5/1921 | United Kingdom | 439/859 |

*Primary Examiner*—David Pirlot
*Attorney, Agent, or Firm*—Joseph Scafetta, Jr.

[57] ABSTRACT

In a contact device for making an electrically conductive connection between a conductor and a contact stud of an ECG electrode, a spring element serves as a contact part and has an apertured plate with an aperture therethrough. The apertured plate with the aperture is arranged in front of contact zones of the spring element. The diameter of the aperture is selected such that only a contact stud with a head which does not exceed a permissible maximum diameter is insertable into the contact device through the apertured plate.

6 Claims, 2 Drawing Sheets

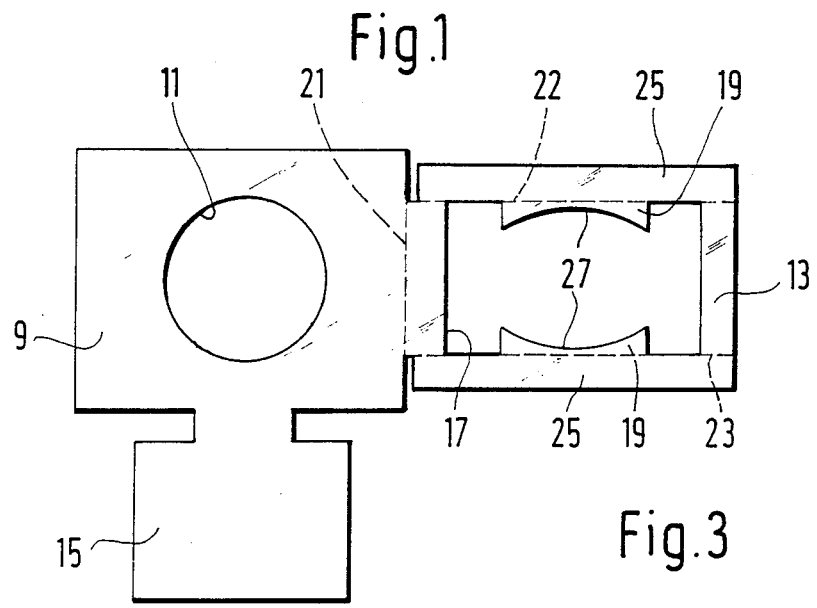
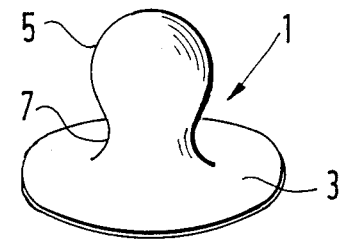
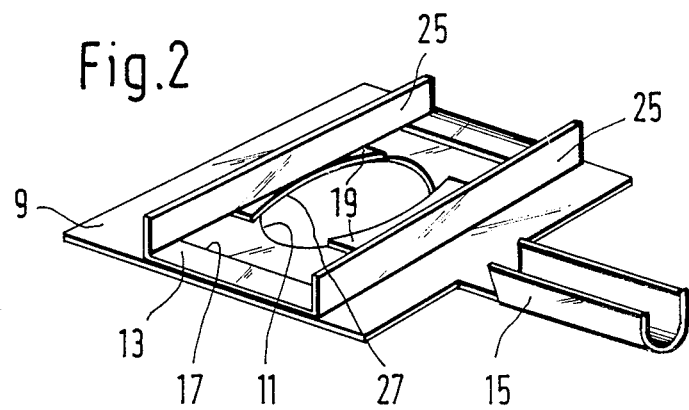

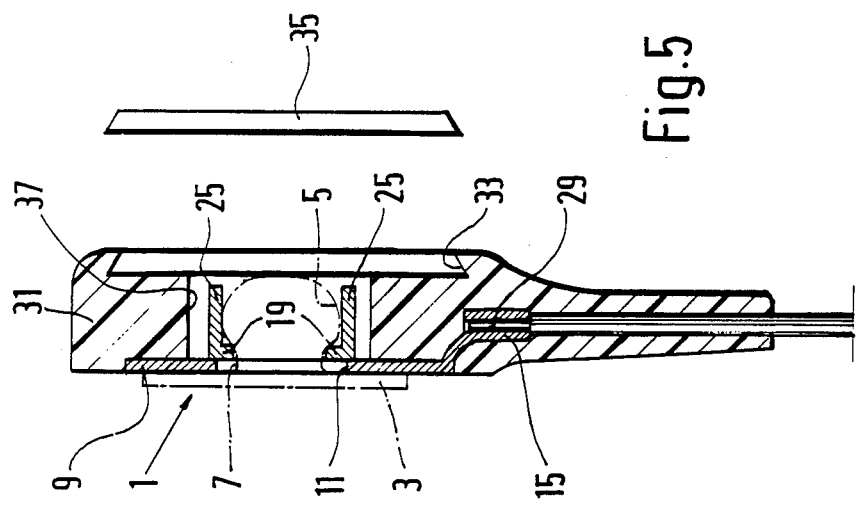
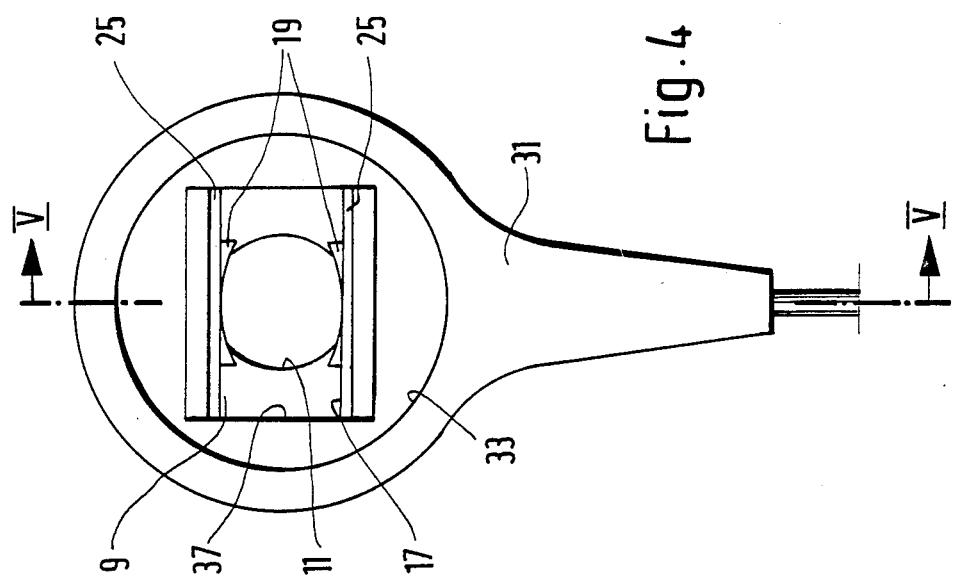

CONTACT DEVICE FOR MAKING AN ELECTRICALLY CONDUCTIVE CONNECTION

BACKGROUND OF THE INVENTION

1. Field of the Invention

The invention relates to a contact device for making an electrically conductive connection between a conductor and a contact stud, for example a contact stud of an ECG electrode.

2. Description of the Related Art

In a contact device of this kind known from West German Patent No. 3,106,594, the spring element serving as a contact part is in the form of a ring which is slit lengthwise and has a constricted part for engagement with the contact stud. The ring-shaped spring element is arranged in the associated holder consisting of an insulating material in such a way that, in the area of the lengthwise slit of the spring element which separates the ring halves, a certain spacing from the wall of the holder is available for spring deflection of the pertinent spring element areas which spring outwardly.

In the known solution, reliability of operation is only guaranteed if the diameter of the contact stud which is to be contacted matches the dimensions of the contact means very well. More particularly, the forcing of a contact stud which is too large into the contact means results in permanent deformations of the spring element and/or the holder if the available space for spring deflection between the holder and the spring element is insufficient.

SUMMARY OF THE INVENTION

The object underlying the invention is to provide a contact means of the kind in question with which there is no danger of the contact means being damaged by connection of a contact stud having a diameter which is too large.

In accordance with the invention, this object is accomplished by a contact means having a contact stud with a recessed section located behind its round head portion, said contact means comprising a holder made of an electrically insulating material for supporting a contact part which, in order to make a push-button-type snap-in connection with the contact stud, is in the form of an integral spring element with contact zones for resiliently snapping into the recessed section of the contact stud. The contact means is characterized in that the spring element has an apertured plate having an aperture with a diameter which is adapted to that of the head portion of the largest contactable contact stud, and in that the contact zones are arranged on a plate-shaped extension of the apertured plate, said extension being bent back towards the apertured plate in such a way that its contact zones are aligned with the aperture of the apertured plate.

In accordance with the invention, the spring element serving as the contact part comprises an apertured plate with an aperture of defined size which is adapted to the diameter of the largest contact stud which can be contacted in an operationally reliable manner. Therefore, when the spring element is embedded in the insulating holder in such a way that the apertured plate faces the contact stud which is to be inserted and the contact zones are located behind the apertured plate, a safety barrier preventing insertion of a contact stud which is too large is formed by the apertured plate. Hence, the danger of the contact means becoming damaged by an attempt to connect a contact stud which is too large is excluded from the start because insertion of such a contact stud is prevented by the apertured plate of the contact part.

In an advantageous embodiment, the apertured plate has a rectangular, preferably square contour. On one side, the contour is defined by the straight bending line along which the extension of the apertured plate forming the contact zones is bent. In addition, a connection lug for connection with the conductor is integrally formed on the apertured plate at one of the side edges of the apertured plate extending transversely to the bending line.

In a further embodiment, the extension of the apertured plate provided for formation of the contact zones comprises a rectangular, planar metal plate with a central cut-out section for passage of the contact stud therethrough. The inside width of the cut-out section is reduced in regions thereof by opposed contact tongues which project towards each other. These tongues are adapted to snap resiliently into the recessed section of the contact stud.

In another advantageous embodiment, the spring element has two parallel spring legs which are connected to each other at both ends and extend over the aperture of the apertured plate. Since the spacing between the spring legs is smaller than the diameter of the aperture, the spring legs contact the head portion of the inserted contact stud in a resilient manner.

The invention will be explained in further detail below with reference to an embodiment shown in the drawings.

BRIEF DESCRIPTION OF THE DRAWINGS

FIG. 1 is a plan view of an integral, unbent stamped part made of sheet metal which in the bent state forms the contact part of an embodiment of the contact means;

FIG. 2 is a perspective view of the contact part bent from the stamped part of FIG. 1;

FIG. 3 is a perspective view of a contact stud for use in the contact means;

FIG. 4 is a rear view of the embodiment containing the contact part of FIG. 2, without the rear cover; and FIG. 5 is a cross-sectional view taken along line V—V of FIG. 4 with the cover shown in the lifted-off state.

DETAILED DESCRIPTION OF THE PREFERRED EMBODIMENT

FIG. 3 shows a round contact stud 1 of an electrocardiogram electrode. The contact stud 1 may be a separate part of the ECG electrode of the conventional kind, not shown, or it may, together with the underside of its plate-shaped foot portion 3, itself form the electrode surface. The contact stud 1 has a spherical head portion 5 and a recessed section 7, i.e., a section 7 whose diameter is smaller than the maximum diameter of the head portion 5, which joins the head portion 5 with the foot portion 3.

A stamped part shown in FIG. 1 is integrally stamped out of a spring sheet metal which is suitable for contacting purposes and has a first main portion in the form of a rectangular apertured plate 9 with an aperture 11 located at the center thereof. An extension 13, similarly of rectangular configuration, adjoins one side edge of the apertured plate 9, at the side edge located on the right in FIG. 1, as a second main portion of the stamped part. A prolongation 15 adjoins the lower side edge, in accordance with FIG. 1, of the apertured plate 9, as a third main portion of the stamped part.

The extension 13 of the stamped part of FIG. 1 has a more or less rectangular, central cut-out section 17 whose inside width is reduced in the central region thereof by contact tongues 19 of identical design which protrude towards each other. Dashed lines in FIG. 1 indicate bending lines. A first bending line 21 at the point of connection between the apertured plate 9 and the extension 13, at the pertinent side edge of the apertured plate 9, defines the contour of the apertured plate 9. Two further bending lines 22 and 23 which run perpendicularly to bending line 21 extend on the extension 13 along the upper and lower edges, respectively, in accordance with FIG. 1, of the cut-out section 17.

The spring element of the contact means shown in the finished state in FIG. 2 is made by bending the stamped part of FIG. 1. To this end, the extension 13 is bent at bending line 21 and folded back into abutment with the apertured plate 9. Also, lateral spring legs 25 are formed by being placed up-right out of the plane of the plate along bending lines 22 and 23. As shown in FIG. 2 illustrating the finished spring element, the spring legs 25 protrude parallel to each other generally perpendicularly out of the plane of the apertured plate 9 and the extension 13 and extend parallel to each other and substantially tangentially over the aperture 11 of the apertured plate 9. The spacing between the spring legs 25 is somewhat smaller than the diameter of the aperture 11. Its inside diameter is additionally narrowed by the contact tongues 19 located at the edges of the aperture 11. The contact tongue edges 27 facing each other are of an arcuate configuration in approximation to the contour of the aperture 11. As is also shown in FIG. 2, the prolongation 15 of the apertured plate 9 is bent to form a connection lug to which a conductor 29 (see FIG. 5) can be connected by crimping or soldering.

FIGS. 4 and 5 show the contact part embedded by an injection molding process in a holder 31 made of an insulating material, for example, an elastic, thermoplastic PVC material. To enable the spring element shown in FIG. 2 and serving as the contact part to be fixed in the injection molding die, the holder 31 is formed in such a way that it has an opening 33 on its upper side, i.e., that side which, after the spring element in embedded therein, is opposite its apertured plate 9. This opening 33 is closable by a marking cover 35 (see FIG. 5) in the manner customary with such contact means. As similarly shown in FIG. 5, the spring element is embedded in a central passage 37 in holder 31 in such a way that the apertured plate 9 forms the outer termination of passage 37 on the side opposite the opening 33. The spring legs 25 extend in passage 37 away from the apertured plate 9 in the direction towards the opening 33.

FIG. 5 shows how the contact stud 1 indicated by a dashed line is secured in passage 37 in a push-button-type manner by the contact tongues 19 engaging its recessed section 7 and how it is contacted by means of the contact tongues 19 and the spring legs 25 resting against the head portion 5. Insertion of a contact stud 1 with a head portion 5 whose diameter is larger than that of the aperture 11 of the apertured plate 9 is not possible because the apertured plate 9 forms the outer termination of the passage 37 in the holder 31 of the contact means. Therefore, the danger of the contact means becoming permanently deformed by improper use of contact studs 1 which are too large is excluded.

All of the features mentioned in the above description and also those apparent from the drawings only are to be construed as further developments within the scope of the invention even if they are not specially emphasized and, in particular, are not recited in the claims appended hereto.

What is claimed is:

1. Contact means for making an electrically conductive connection between a conductor and a contact stud having a recessed section located behind a rounded head portion, said contact means comprising:

a holder made of an electrically insulating material for supporting a contact part which in order to make a push-button-type snap-in connection with the contact stud is in the form of an integral spring element with contact zones for resiliently snapping into the recessed section of the contact stud;

wherein the spring element has an apertured plate having an aperture with a diameter which is adapted to that of the head portion of the contact stud;

wherein the contact zones are arranged on a plate-shaped extension of the apertured plate, said extension being bent back towards the apertured plate in such a way that its contact zones are aligned in approximation with an inner contour of the aperture of the apertured plate;

wherein said extension of the apertured plate provided for formation of the contact zones is a rectangular, planar metal plate with a central cut-out section enabling passage of the head portion of the contact stud therethrough, an inside diameter of the cut-out section being reduced in regions thereof by opposed contact tongues projecting towards each other; and characterized in that, in order to form spring legs contacting the head portion of the inserted contact stud in a resilient manner, longitudinal edges of the extension adjacent to the projecting contact tongues are bent out of a plane of the extension about bending lines which extend at right angles to a bending line laterally defining the apertured plate.

2. Contact means for making an electrically conductive connection between a conductor and a contact stud having a recessed section located behind a rounded head portion, said contact means comprising:

a holder made of an electrically insulating material for supporting a contact part which in order to make a push-button-type snap-in connection with the contact stud is in the form of an integral spring element with contact zones for resiliently snapping into the recessed section of the contact stud;

wherein the spring element has an apertured plate having an aperture with a diameter which is adapted to that of the head portion of the contact stud;

wherein the contact zones are arranged on a plate-shaped extension of the apertured plate, said extension being bent back towards the apertured plate in such a way that its contact zones are aligned in approximation with an inner contour of the aperture of the apertured plate;

wherein said apertured plate is a planar, rectangular metal plate which is defined at one side edge by a straight bending line along which the extension of the apertured plate is bent back, and which has a prolongation formed on one of its other side edges extending transversely to the bending line as a lug for connection with the conductor;

wherein said extension of the apertured plate provided for formation of the contact zones is a rectangular, planar metal plate with a central cut-out section enabling passage of the head portion of the contact stud therethrough, an inside diameter of the cut-out section being reduced in regions thereof by opposed contact tongues projecting towards each other; and characterized in that, in order to form spring legs contacting the head portion of the inserted contact stud in a resilient manner, longitudinal edges of the extension adjacent to the projecting contact tongues are bent out of a plane of the extension about bending lines which extend at right angles to the bending line laterally defining the apertured plate.

3. Contact means for making an electrically conductive connection between a conductor and a contact stud having a recessed section located behind a rounded head portion, said contact means comprising:

a holder made of an electrically insulating material for supporting a contact part which in order to make a push-button-type snap-in connection with the contact stud is in the form of an integral spring element with contact zones for resiliently snapping into the recessed section of the contact stud;

wherein the spring element has an apertured plate having an aperture with a diameter which is adapted to that of the head portion of the contact stud;

wherein the contact zones are arranged on a plate-shaped extension of the apertured plate, said extension being bent back towards the apertured plate in such a way that its contact zones are aligned in approximation with an inner contour of the aperture of the apertured plate;

wherein said apertured plate is a planar, rectangular metal plate which is defined at one side edge by a straight bending line along which the extension of the apertured plate is bent back, and which has a prolongation formed on one of its other side edges extending transversely to the bending line as a lug for connection with the conductor; and characterized in that, in order to form spring legs contacting said head portion of an inserted contact stud in a resilient manner, longitudinal edges of the extension adjacent to projecting contact tongues are bent out of a plane of the extension about bending lines which extend at right angles to a bending line laterally defining the apertured plate.

4. Contact means as defined in claim 1, wherein edges of the contact tongues which face each other are curved so as to match a rounded shape of the contact stud.

5. Contact means as defined in claim 2, wherein: edges of the contact tongues which face each other are curved so as to match a rounded shape of the contact stud.

6. Contact means as defined in claim 3, wherein: edges of the contact tongues which face each other are curved so as to match a rounded shape of the contact stud.

* * * * *

UNITED STATES PATENT AND TRADEMARK OFFICE
CERTIFICATE OF CORRECTION

PATENT NO. : 4,842,557

DATED : June 27, 1989

INVENTOR(S) : Edwin Muz

It is certified that error appears in the above-identified patent and that said Letters Patent is hereby corrected as shown below:

Cover page, under References Cited, "Daddona et al." should be --Daddona Jr.--

Signed and Sealed this

Seventeenth Day of April, 1990

Attest:

HARRY F. MANBECK, JR.

*Attesting Officer*  *Commissioner of Patents and Trademarks*